US006632970B1

(12) United States Patent

Lyons

(10) Patent No.: US 6,632,970 B1
(45) Date of Patent: Oct. 14, 2003

(54) CATALYTIC HYDROGENATION TO REMOVE GAS FROM X-RAY TUBE COOLING OIL

(75) Inventor: Robert J. Lyons, Wauwatosa, WI (US)

(73) Assignee: General Electric Company, Schenectady, NY (US)

( * ) Notice: Subject to any disclaimer, the term of this patent is extended or adjusted under 35 U.S.C. 154(b) by 0 days.

(21) Appl. No.: 09/474,454

(22) Filed: Dec. 29, 1999

Related U.S. Application Data

(62) Division of application No. 09/108,452, filed on Jul. 1, 1998, now Pat. No. 6,123,456.

(51) Int. Cl.[7] .............................. C07C 5/02; H01B 3/22

(52) U.S. Cl. ........................ 585/275; 585/277; 585/6.3; 585/6.6; 252/570; 252/571; 252/572

(58) Field of Search .......................... 585/6.3, 6.6, 254, 585/257, 2, 277, 275; 208/14; 252/570, 571, 572

(56) References Cited

U.S. PATENT DOCUMENTS

| | | | | |
|---|---|---|---|---|
| 2,326,324 A | * | 8/1943 | Berger et al. | 252/572 |
| 3,036,010 A | * | 5/1962 | Freier et al. | 585/6.6 |
| 4,469,849 A | * | 9/1984 | Murrer et al. | 525/339 |
| 5,086,449 A | * | 2/1992 | Furbee et al. | 378/200 |
| 5,222,118 A | * | 6/1993 | Gerth | 378/200 |
| 5,357,555 A | * | 10/1994 | Gerth | 378/200 |

FOREIGN PATENT DOCUMENTS

| | | | |
|---|---|---|---|
| DE | 4414687 A1 | * | 11/1995 |
| DE | 4414688 A1 | * | 11/1995 |
| JP | 62-274599 A | * | 11/1989 |
| JP | 9-45492 A | * | 2/1997 |

* cited by examiner

*Primary Examiner*—Walter D. Griffin
(74) *Attorney, Agent, or Firm*—Dougherty, Clements & Hofer; Tracey R. Loughlin

(57) ABSTRACT

The present invention deals with the catalytic hydrogenation of fluid used to cool and dielectrically insulate an x-ray generating device within an x-ray system. According to the present invention, a method and apparatus are provided for hydrogenating fluid that has been exposed to x-rays to reduce the amount of $H_2$ gas, free hydrogen atoms and unsaturated molecules in the fluid. The method comprises exposing the fluid within the x-ray system to a catalytically effective amount of catalyst. The catalyst operates in temperatures in the range of about 10–300° C. and pressures in the range of about 0.1–30 atmospheres. The catalyst may comprise a solid, non-soluble catalyst, a soluble catalyst, or a combination of both. A suitable solid, non-soluble catalyst comprises Group VIII elements and their compounds. Group VIII elements comprise iron, cobalt, nickel, ruthenium, rhodium, palladium, osmium, iridium and platinum. The catalytically effective amount of solid catalyst ranges from about 1–100 $cm^2$ of surface area of solid catalyst per liter of fluid. Additionally, a suitable soluble catalyst may be added to the fluid and may comprise tris(triphenylphosphine) rhodium (I) chloride, precious metals in solution such as $HRu(C_2H_4)(C_6H_4PPh_2)(PPh_3)_2)$, Wilkinson's catalyst which comprises a rhodium, chromium, phosphorus triphenyl chloride compound, and other similar compounds. A catalytically effective amount of soluble catalyst may comprise from about 0.01–1 gram per liter of fluid. The fluid may comprise about 99.7% hydrocarbon, about 0.1% soluble catalyst, and the remainder comprising conditioning additives. The hydrocarbon preferably comprises about 99.7% hydrogenated light naphthenic petroleum distillates.

12 Claims, 2 Drawing Sheets

CATALYTIC HYDROGENATION TO REMOVE GAS FROM X-RAY TUBE COOLING OIL

The present invention is a divisional application of U.S. patent application Ser. No. 09/108,452 filed Jul. 1, 1998, now U.S. Pat. No. 6,123,456.

FIELD OF THE INVENTION

The present invention relates to dielectric fluid for cooling and electrically insulating x-ray tubes, and more particularly, to a system and method for catalytic hydrogenation of x-ray tube dielectric fluid that is subject to chemical breakdown due to exposure to x-ray radiation.

BACKGROUND

A dielectric oil is typical fluid used to cool and electrically insulate an x-ray tube. The dielectric oil is subject to chemical breakdown, however, upon exposure to x-ray radiation. After exposure to x-rays, the dielectric oil comprises unsaturated hydrocarbon molecules, free hydrogen atoms, and $H_2$ gas. The formation of the $H_2$ gas is disadvantageous as it may reduce the electrical insulating characteristics of the dielectric oil and may interfere with the transmission of the x-rays. Thus, it is desirable to reduce and/or eliminate the formation of $H_2$ gas in the x-ray tube dielectric fluid.

Typically, an x-ray beam generating device, referred to as an x-ray tube, comprises dual electrodes of an electrical circuit in a vacuum chamber within a cylindrical vacuum vessel envelope. The vacuum vessel envelope typically comprises a glass tube or a cylinder made of metal. One of the electrodes is a cathode assembly which is positioned in a spaced relationship to a rotating, disc-shaped target that comprises the anode assembly. Upon energization of the electrical circuit connecting the electrodes, the cathode assembly produces a supply of electrons which are accelerated and focused to a thin beam. The thin beam of very high velocity electrons is directed parallel to the axis of the vacuum vessel envelope to strike a section of the rotating target anode. The kinetic energy produced by the beam of electrons striking the surface of the section of the target anode, which comprises a material such as a refractory metal, is converted to electromagnetic waves of very high frequency. These high frequency electromagnetic waves are x-rays. The surface of the target anode is typically angled, which helps to direct the x-rays out the side of the vacuum vessel envelope. After exiting the vacuum vessel envelope, the x-rays are directed to penetrate an object, such as human anatomical parts for medical examination and diagnostic procedures. Further, industrial x-ray tubes may be used, for example, to inspect metal parts for cracks or for inspecting the contents of luggage at airports.

The x-ray generating device is ordinarily surrounded by a casing filled with a circulating fluid, which helps to minimize the operating temperature of the x-ray tube by absorbing heat. Dielectric fluid for x-ray generating devices typically operates at temperatures in the range of about 20–70° C. This very high operating temperature is the result of the thermal energy transferred from the tube to the fluid due to the high electric current required to generate and accelerate the electrons, the kinetic energy produced by the electrons hitting the target, and the x-rays themselves. Dielectric oil is typically the fluid utilized to carry the heat away from the x-ray tube, as dielectric oil can absorb and carry away a large amount of thermal energy.

The circulating fluid used to cool the x-ray tube additionally has dielectric properties that electrically insulate the tube. A typical x-ray tube utilizes a tremendous amount of energy to generate x-rays. A typical x-ray tube may require from about 120,000 to 140,000 volts and from about 40–400 milliamps, which produces up to about 40 kilowatts of power. Whereas this very high electrical charge exists within the x-ray tube, the casing is at ground potential. Without an electrical insulator between the tube and the casing, the electrical charge within the tube would tend to arc to the casing, similar to lightning arcing from the clouds to the earth. So, if there is a bad dielectric insulator around the tube, the voltage can break through the tube and ground to the casing. The break through of the voltage can result not only in the charring of the circulating dielectric, but also in the cracking of the vacuum envelope of the tube. Thus, the dielectric properties of the circulating fluid must be maintained to insure the reliability of the x-ray tube.

The dielectric properties of the circulating fluid, however, are negatively affected by the x-rays generated by the tube. The x-ray radiation breaks chemical bonds within the dielectric fluid. Typically, the x-ray radiation breaks carbon-carbon (C—C) and carbon-hydrogen (C—H) bonds, resulting in the release of hydrogen atoms. The free hydrogen atoms combine into diatomic hydrogen or $H_2$, which is a gas that forms bubbles within the circulating dielectric fluid. As the amount of $H_2$ in the dielectric fluid increases, the size of the bubbles can increase and displace the dielectric fluid. The high voltage within the x-ray tube can then arc across the bubble and short out on the casing. Thus, the formation of gas bubbles caused by the break down of the dielectric fluid by the x-ray radiation inhibits the electrical insulating properties of the dielectric fluid, possibly leading to high voltage arcing and the failure of the x-ray tube.

Many sources of gas within the dielectric fluid can be removed by vacuum treating the fluid prior to its use. In this case, however, the gas is produced during the x-ray generating process. As such, vacuum treating the dielectric fluid prior to its use will not eliminate this problem. Thus, there is a need for a method to eliminate the gas produced within the dielectric fluid during the x-ray process.

SUMMARY OF THE INVENTION

According to the present invention, a method for hydrogenating a dielectric fluid comprising a hydrocarbon that upon exposure to x-rays releases hydrogen atoms, comprises exposing the dielectric fluid to an effective amount of a catalyst system that promotes the recombination of the hydrogen atoms with the hydrocarbon. The dielectric fluid is employed as a cooling element for an x-ray generating device, and preferably comprises hydrogenated napthacene. The catalyst system operates in temperatures in the range of about 10–300° C. and pressures in the range of about 0.1–30 atmospheres. The catalyst system may comprise either a solid, non-soluble catalyst or a soluble catalyst.

A suitable solid catalyst may comprise a Group VIII element or a compound of a Group VIII element. The effective amount of solid catalyst is at least 1 $cm^2$ surface area per liter of the dielectric fluid up to about 100 $cm^2$, and preferably 10 $cm_2$ surface area per liter of the dielectric fluid. The solid catalyst may comprise an element selected from the group consisting of ruthenium, rhodium, palladium, osmium, iridium and platinum, or more preferably solid catalyst comprises at least one of palladium and platinum.

A suitable soluble catalyst is in solution with the dielectric fluid, wherein the effective amount of soluble catalyst is at least 0.01 gram per liter of the dielectric fluid up to about 1 gram per liter of dielectric fluid. The soluble catalyst may comprise tris(triphenylphosphine) rhodium (I) chloride, precious metals in solution such as $HRu(C_2H_4)(C_6H_4PPh_2)(PPh_3)_2)$, Wilkinson's catalyst which comprises a rhodium, chromium, phosphorus triphenyl chloride compound, and other similar compounds.

In another embodiment, a system for hydrogenating dielectric fluid subject to the formation of hydrogen gas and unsaturated hydrocarbons due to x-ray exposure from an x-ray generating device, comprises an effective amount of a catalyst system positioned within the x-ray generating device to interact with the dielectric fluid for promoting the reaction of the hydrogen gas with the unsaturated hydrocarbons within the dielectric fluid to reduce the amount of hydrogen gas in the dielectric fluid. The hydrogenating system preferably comprises an x-ray system. The catalyst system operates in temperatures in the range of about 10–300° C. and pressures in the range of about 0.1–30 atmospheres. The catalyst system may comprise a solid catalyst or a soluble catalyst. A suitable solid catalyst comprises a Group VIII element or a compound of a Group VIII element. The solid catalyst may comprise an element selected from the group consisting of ruthenium, rhodium, palladium, osmium, iridium and platinum, or more preferably solid catalyst comprises at least one of palladium and platinum. The effective amount of solid catalyst is at least 1 $cm^2$ surface area per liter of the dielectric fluid up to about 100 $cm^2$, and preferably 10 $cm^2$ surface area per liter of the dielectric fluid. A suitable soluble catalyst is in solution with the dielectric fluid, wherein the effective amount of catalyst is at least 0.01 gram per liter of the dielectric fluid up to about 1 gram per liter of dielectric fluid. The soluble catalyst may comprise tris(triphenylphosphine) rhodium (I) chloride, precious metals in solution such as $HRu(C_2H_4)(C_6H_4PPh_2)(PPh_3)_2)$, Wilkinson's catalyst which comprises a rhodium, chromium, phosphorus triphenyl chloride compound, and other similar compounds.

In yet another embodiment, an x-ray system, comprises an x-ray generating device for producing x-rays, a dielectric fluid circulated about the device to cool and electrically insulate the device, wherein the fluid comprises a hydrocarbon that upon exposure to the x-rays releases hydrogen atoms, and an effective amount of a catalyst system, in communication with the dielectric fluid, that promotes the recombination of the hydrogen atoms with the hydrocarbon. The catalyst system operates in temperatures in the range of about 10–300° C. and pressures in the range of about 0.1–30 atmospheres. The catalyst system may comprise a solid catalyst or a soluble catalyst. A suitable solid catalyst comprises a Group VIII element or a compound of a Group VIII element. The solid catalyst may comprise an element selected from the group consisting of ruthenium, rhodium, palladium, osmium, iridium and platinum, or more preferably solid catalyst comprises at least one of palladium and platinum. The effective amount of solid catalyst is at least 1 $cm^2$ surface area per liter of the dielectric fluid up to about 100 $cm^2$, and preferably 10 $cm^2$ surface area per liter of the dielectric fluid. A suitable soluble catalyst is in solution with the dielectric fluid, wherein the effective amount of catalyst is at least 0.01 gram per liter of the dielectric fluid up to about 1 gram per liter of dielectric fluid. The soluble catalyst may comprise tris(triphenylphosphine) rhodium (I) chloride, precious metals in solution such as $HRu(C_2H_4)(C_6H_4PPh_2)(PPh_3)_2)$, Wilkinson's catalyst which comprises a rhodium, chromium, phosphorus triphenyl chloride compound, and other similar compounds.

Finally, the present invention discloses a dielectric fluid comprising a hydrocarbon component, a hydrogenating catalyst system, and wherein the dielectric fluid is suitable for use as a cooling element for an x-ray generating device. The dielectric fluid further comprises about 99.7% hydrocarbon, about 0.1% catalyst system, and the remainder comprising conditioning additives. The hydrocarbon comprises about 99.7% hydrogenated light naphthenic petroleum distillates. The hydrogenating catalyst system comprises tris(triphenylphosphine) rhodium (I) chloride, precious metals in solution such as $HRu(C_2H_4)(C_6H_4PPh_2)(PPh_3)_2)$, Wilkinson's catalyst which comprises a rhodium, chromium, phosphorus triphenyl chloride compound, and other similar compounds.

DETAILED DESCRIPTION OF THE INVENTION

According to one aspect of the present invention, a method of hydrogenating a dielectric fluid, comprising a hydrocarbon that upon exposure to x-rays releases hydrogen atoms, comprises exposing the dielectric fluid to an effective amount of a catalyst system that promotes the recombination of the hydrogen with the dielectric fluid.

In another aspect of the present invention, a system for hydrogenating dielectric fluid subject to the formation of hydrogen gas and unsaturated hydrocarbons due to x-ray exposure in a x-ray generating device, comprises an effective amount of a catalyst system positioned within the x-ray generating device to interact with the dielectric fluid for promoting the reaction of the hydrogen gas with the unsaturated hydrocarbons within the dielectric fluid to reduce the amount of hydrogen gas in the dielectric fluid.

In a further aspect of the present invention, an x-ray system comprises an x-ray generating device for producing x-rays, a dielectric fluid circulated about the device to cool and electrically insulate the device, where the fluid comprises a hydrocarbon that upon exposure to x-rays releases hydrogen atoms, and an effective amount of a catalyst system, in communication with the dielectric fluid, that promotes the recombination of the hydrogen atoms with the hydrocarbon.

In yet another aspect of the invention, a dielectric fluid comprises a hydrocarbon component, a hydrogenating catalyst, and the dielectric fluid is suitable for use as a cooling element for an x-ray generating device. The dielectric fluid may comprise about 99.7% hydrocarbon, about 0.1% catalyst system, and the remainder comprising conditioning additives. Further, the hydrocarbon may comprise about 99.7% hydrogenated light naphthenic petroleum distillates and the catalyst may comprise tris (triphenylphosphine) rhodium (I) chloride.

Figure 1:
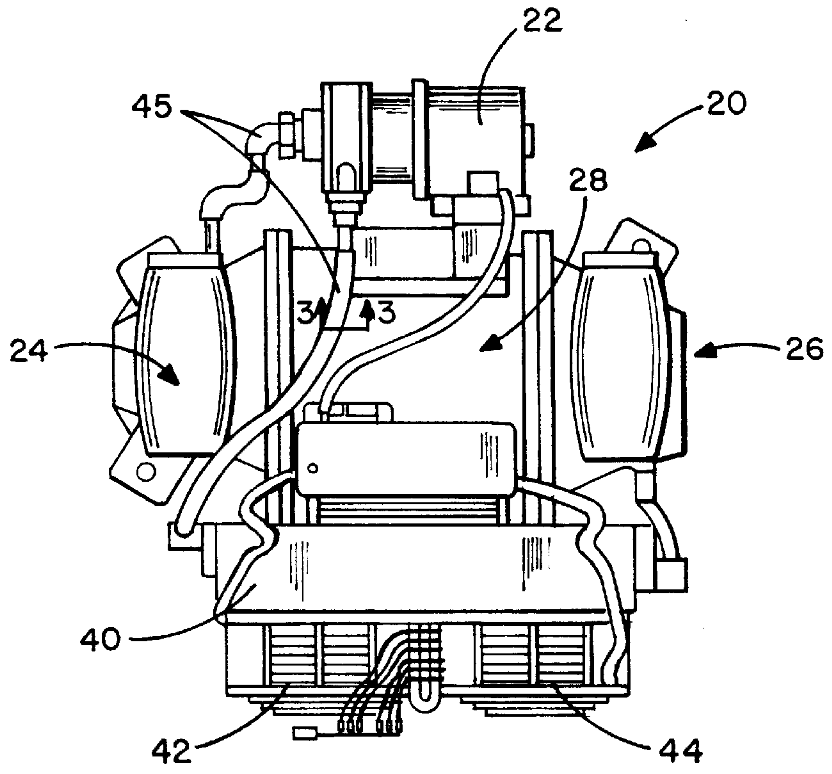
FIG. 1 is a plan view of a representative x-ray system having an x-ray generating device or x-ray tube positioned therein.
Figure 2:
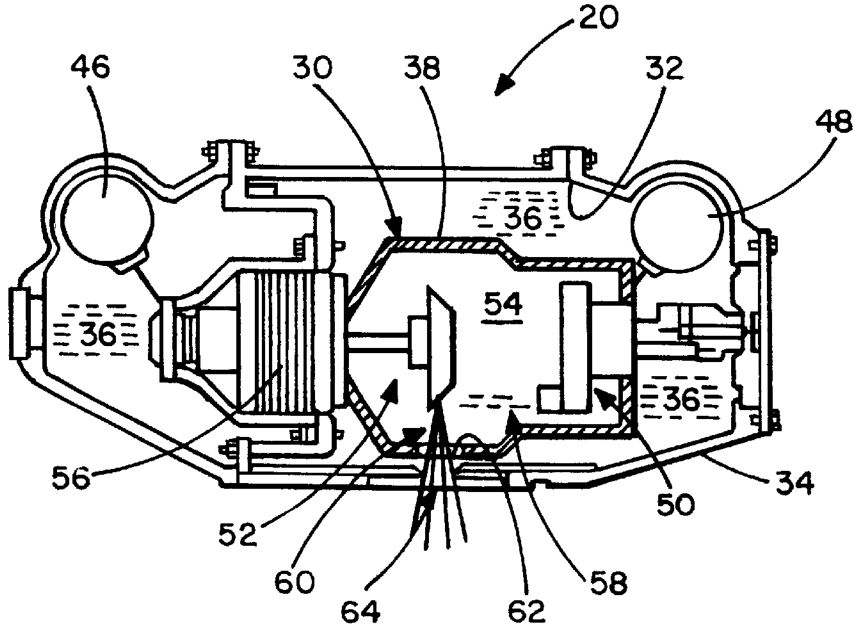
FIG. 2 is a sectional view with parts removed of the x-ray system of FIG. 1 including the x-ray generating device.

Referring to FIGS. 1 and 2, the present invention is typically utilized in an x-ray system 20. A typical x-ray system 20 comprises a fluid pump 22, an anode end 24, a cathode end 26, a center section 28 positioned between the anode end and cathode end, which contains an x-ray generating device or x-ray tube 30 (FIG. 2). The x-ray generating device 30 is enclosed in a fluid chamber 32 within lead-lined casing 34 (FIG. 2). Chamber 32 is typically filled with fluid 36, such as a dielectric fluid, but other fluids may be utilized. Fluid 36 circulates through system 20 to cool x-ray generating device 30 and also to insulate casing 34 from the high electrical charges within vacuum vessel envelope 38 of the device. A radiator 40 for cooling fluid 36 is positioned to one side of center section 28 and may have operatively connected fans 42 and 44 for providing cooling air flow over the radiator as the hot fluid 36 circulates through it. Pump 22 is provided to circulate fluid 36 through system 20, fluid hoses 45 and through radiator 40, etc. Electrical connections are provided in anode receptacle 46 and cathode receptacle 48 (FIG. 2) for energizing system 20.

Referring to FIG. 2, x-ray system 20 comprises casing 34 preferably made with aluminum and lined with lead to block x-ray passage. X-ray generating device or x-ray tube 30 within system 20 typically comprises a cathode assembly 50 and a rotating, disc-like target anode assembly 52 within a vacuum chamber 54 in a vacuum vessel envelope 38. A stator 56 is positioned outside vacuum vessel envelope 38 inside lead-lined casing 34 relative to rotating disc-like target anode assembly 52. Upon energization of the electrical circuit connecting cathode assembly 50 and anode assembly 52, a stream of electrons 58 are directed and accelerated toward the anode assembly. The stream of electrons 58 strikes the surface of anode assembly 52 and produces high frequency electromagnetic waves or x-rays 60. X-rays 60 are directed through vacuum chamber 54 and out of vacuum vessel envelope 38 through transmissive window 62. Alternatively, if vacuum vessel envelope 38 is glass, Pyrex or a material with low attenuation of diagnostic levels of radiation (≧60,000 electronvolts), then no separate window 62 is required (not shown). The x-rays 60 proceed through fluid 36 between x-ray generating device 30 and casing 34 and through window 64, which comprises an x-ray transmissive material, such as beryllium. Window 64 is operatively formed in casing 34 relative to transmissive window 62 in vacuum vessel envelope 38. Thus, x-rays 60 are emitted from system 20 toward an object.

Vacuum vessel envelope 38 is constructed of a material that is able to structurally handle the loads generated by vacuum chamber 54 and rotating anode assembly 52 in a high temperature environment. Vacuum vessel envelope 38 is formed using well-known manufacturing methods, and as mentioned above, may be formed of x-ray transmissive material such as glass or Pyrex, or a non-x-ray transmissive material such as stainless steel or copper. Vacuum vessel envelope 38 must be able to withstand the high temperatures of the x-ray generating device 30 environment. For example, anode 52 operates from about 500–1800° C., cathode 50 up to about 600° C. and vacuum vessel envelope 38 operates up to about 120° C. Vacuum vessel envelope 38 is heated by the operating temperatures within chamber 54, and further by absorption of x-rays 60, deflected electrons and lower energy electromagnetic waves (not shown) within the vacuum chamber that have not attained enough energy to become x-rays.

Fluid 36 is typically a dielectric fluid capable of electrically insulating casing 34 from the very high voltages and currents within x-ray tube 30 and also capable of cooling the tube. Fluid 36 provides electrical insulation from voltages which may range from about 80 KV to 160 KV and currents which may range from about 250 to 400 mA. Additionally, fluid 36 is capable of cooling x-ray tube 30 and maintaining the tube at a predetermined operating temperature by absorbing heat from the x-ray generation process. Such dielectric fluids may comprise hydrogenated naphthacene compounds, as well as other hydrogenated polyaromatic compounds.

As x-rays 60 pass through fluid 36, the radiation from the x-rays tends to cause a chemical breakdown of the fluid molecule. Exposure to x-rays 60 tends to break the carbon-carbon (C—C) bonds and carbon-hydrogen (C—H) bonds, producing an unsaturated molecule and free hydrogen atoms which tend to form $H_2$ gas. By way of example for a fluid 36 comprising hydrogenated naphthacene compounds, it is believed the reaction proceeds as follows:

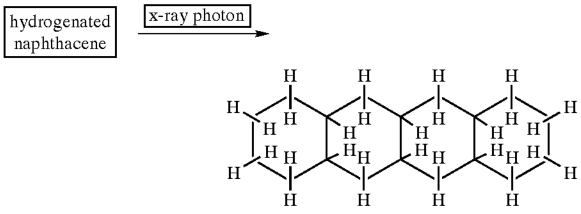

Results in:

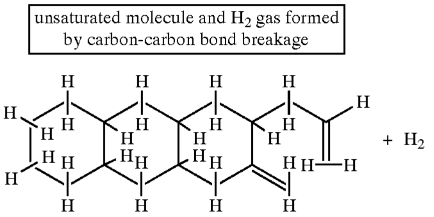

The chemical breakdown of the hydrogenated napthacene is problematic because the $H_2$ gas produces bubbles within fluid 36 and displaces the fluid. The bubbles and fluid displacement reduce the effectiveness of fluid 36 as an electrical insulator, as the electricity may arc through the bubbles to casing 34. Additionally, fluid 36 cannot be pre-treated, such as by vacuum treating, to eliminate the $H_2$ gas as the gas forms during the operation of system 40.

The present invention provides a system and method for advantageously recombining the free hydrogen atoms and $H_2$ gas with the unsaturated molecule produced by exposure to x-ray radiation. A hydrogenation catalyst system 66 is introduced into x-ray system 20 to interact with fluid 36. Catalyst system 66 drives a reaction between the unsaturated molecule and the free hydrogen atoms and $H_2$ gas, resulting in decreasing the amount of unsaturated molecules, free hydrogen atoms and $H_2$ gas in fluid 36. By way of example for a fluid 36 comprising hydrogenated naphthacene compounds, it is believed the reaction proceeds as follows:

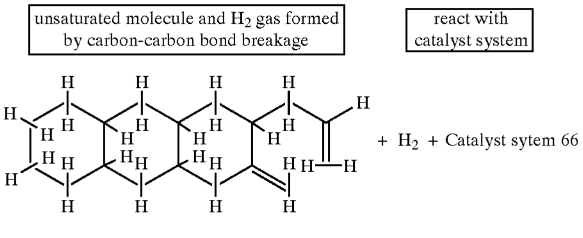

Results in:

hydrogen reabsorbed by unsaturated molecule, thereby reducing/eliminating $H_2$ gas

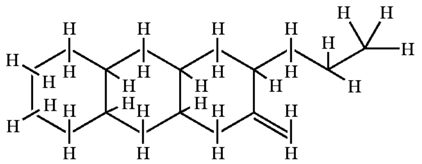

Thus, catalyst system 66 provides a means for returning the free hydrogen atoms to the molecules comprising fluid 36, thereby reversing the formation of the $H_2$ gas and improving the dielectric properties of the fluid.

The present invention is capable of driving the reaction at temperatures in the range of about 10–300° C. and pressures in the range of about 0.1–30 atmospheres. Catalyst 66 thereby advantageously is able to reduce and eventually substantially eliminate $H_2$ gas within fluid 36 at all levels of operating temperatures as well as at ambient when x-ray tube 30 is inactive.

Figure 3:
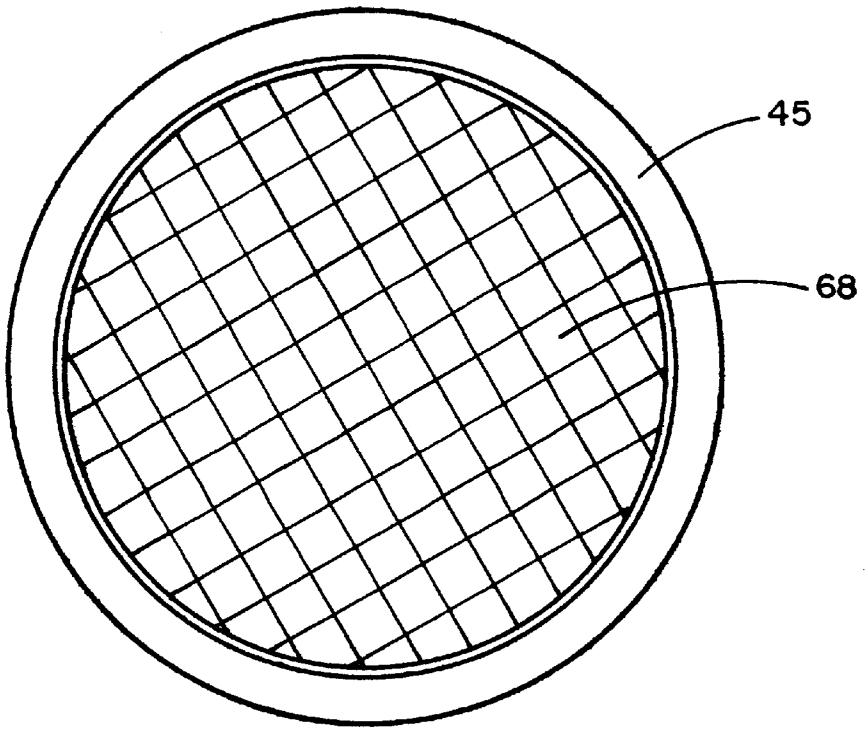
FIG. 3 is a sectional view taken along line 3—3 in FIG. 1.
Figure 4:
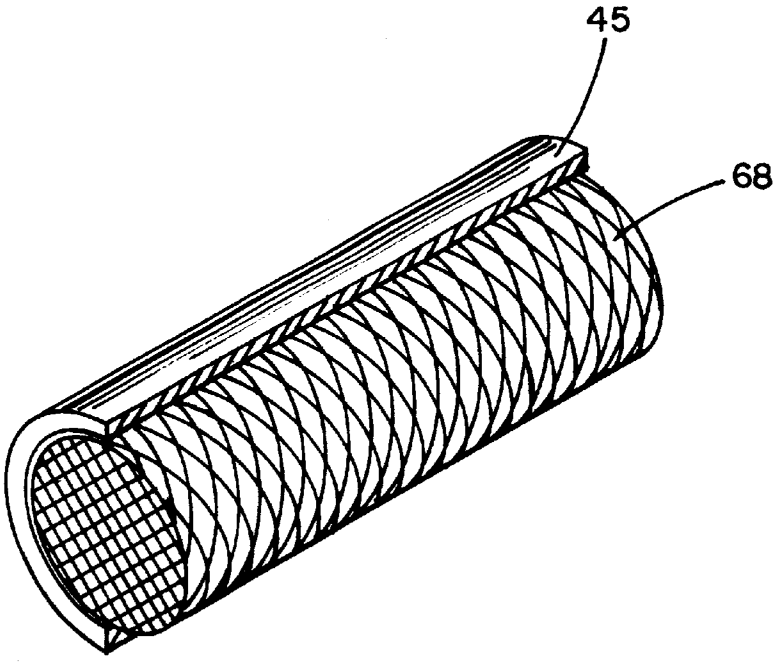
FIG. 4 is a perspective view of a fluid hose with portions removed exposing the solid catalyst.

Catalyst system 66 may be provided either in solution with fluid 36, or as a solid, non-soluble material, or as some combination of both. Referring to FIGS. 3 and 4, solid catalyst 68 is provided within hose 45 within the fluid circulation system, comprising pump 22 and radiator 40. Solid catalyst 68 may comprise a filter-like mesh of strands of the catalyst material. Alternatively, depending on the reaction conditions, solid catalyst 68 may form a lining of the circulation system, such as by a deposition process, or the solid catalyst may be contained within the system whereby fluid 36 circulates over the solid catalyst. A suitable solid catalyst 68 preferably comprises Group VIII elements and their compounds. Group VIII elements comprise iron, cobalt, nickel, ruthenium, rhodium, palladium, osmium, iridium and platinum. Fluid 36, comprising the unsaturated hydrocarbons and hydrogen atoms and $H_2$ gas, interacts with the surface of solid catalyst 68, resulting in the recombination of hydrogen with the unsaturated hydrocarbon thereby reducing the amount of $H_2$ gas in fluid 36.

When using the solid catalyst 68, a catalytically effective amount of the solid catalyst may comprise from about 1–100 $cm^2$, preferably about 10 $cm^2$, of surface area of catalyst per liter of fluid 36. As one skilled in the art will recognize, the range of the effective amount of solid catalyst 68 varies depending upon the type of catalyst used and the type of fluid 36. In this embodiment, solid catalyst 68 may comprise rolled foil, shredded and plated metal, plated lining in casing 34 or within radiator 40, pump 22 or other fluid circulating components. Further, solid catalyst 68 may be a solid material in a porous container, plated metal on a screen or other filter-like device that fluid 36 may circulate through, or other similar devices which would be obvious to one skilled in the art in view of this disclosure.

Alternatively, catalyst system 66 may be provided as a soluble catalyst 70 in solution with fluid 36. For example, a suitable soluble catalyst 70 may comprise tris (triphenylphosphine) rhodium (I) chloride added to fluid 36. Other examples of soluble catalyst 70 in solution with fluid 36 include precious metals in solution such as $HRu(C_2H_4)(C_6H_4PPh_2)(PPh_3)_2)$, Wilkinson's catalyst which comprises a rhodium, chromium, phosphorus triphenyl chloride compound, and other similar compounds. A catalytically effective amount of soluble catalyst 70 may comprise from about 0.01–1 gram per liter of fluid 36. The dielectric fluid may comprise about 99.7% hydrocarbon, about 0.1% soluble catalyst 70, and the remainder comprising conditioning additives. Preferably, the hydrocarbon may comprise about 99.7% hydrogenated light naphthenic petroleum distillates and the catalyst may comprise tris (triphenylphosphine) rhodium (I) chloride. As one skilled in the art will recognize, however, the range of the effective amount of soluble catalyst 70 varies depending upon the type of catalyst used and the type of fluid 36.

One advantageous feature of the present invention provides for decreasing the amount of unsaturated molecules, free hydrogen atoms and $H_2$ gas in fluid 36 both at operating temperatures of the fluid and at ambient temperature, such as when system 20 is idle. When the capability of hydrogenating fluid 36 at ambient temperatures is desired, solid catalyst 68 is preferably palladium, but may comprise platinum, rhodium, iridium, osmium and ruthenium. Similarly, the various soluble catalysts 70 discussed above also are active and drive the desired reaction at ambient temperature. This range of activity beneficially allows the hydrogenation of fluid 36 to occur at low level temperatures where typical commercial hydrogenation catalysts, such as nickel and its compounds, cannot be used.

Thus, the present invention advantageously provides a method and apparatus for catalytic hydrogenation of radiation-damaged fluid 36 used to cool and electrically insulate x-ray tube 30 in x-ray system 20.

Although the invention has been described with reference to these preferred embodiments, other embodiments can achieve the same results. Variations and modifications of the present invention will be apparent to one skilled in the art and the following claims are intended to cover all such modifications and equivalents.

What is claimed is:

1. In an x-ray generation system, a method for hydrogenating a dielectric fluid comprising a hydrocarbon that upon exposure to x-rays releases hydrogen atoms, comprising:

exposing the dielectric fluid in the x-ray generation system to an effective amount of catalyst, operative independent of x-ray energy, that promotes the recombination of the hydrogen atoms with the hydrocarbon, wherein the effective amount of the catalyst comprises at least one of: (1) at least 1 $cm^2$ surface area of a solid catalyst per liter of the dielectric fluid, and (2) at least 0.01 gram of a soluble catalyst per liter of the dielectric fluid.

2. A method of hydrogenating dielectric fluid as recited in claim 1, wherein the dielectric fluid is employed as a cooling element for the x-ray generating system.

3. A method of hydrogenating dielectric fluid as recited in claim 1, wherein the dielectric fluid comprises hydrogenated napthacene.

4. A method of hydrogenating dielectric fluid as recited in claim 1, wherein exposing the dielectric fluid to the catalyst occurs at temperatures in the range of about 10° C.–300° C. and pressures in the range of about 0.1 atmospheres–30 atmospheres.

5. A method of hydrogenating dielectric fluid as recited in claim 1, wherein the catalyst comprises at least one of the following: a Group VIII element and a compound of a Group VIII element.

6. A method of hydrogenating dielectric fluid as recited in claim 1, wherein the effective amount of catalyst comprises about 1 $cm^2$ surface area per liter of the dielectric fluid up to about 100 $cm^2$ surface area per liter of the dielectric fluid.

7. A method of hydrogenating dielectric fluid as recited in claim 1, wherein the catalyst comprises at least one of iron, cobalt, nickel, ruthenium, rhodium, palladium, osmium, iridium and platinum.

8. A method of hydrogenating dielectric fluid as recited in claim 6, wherein the catalyst comprises at least one of palladium and platinum.

9. A method of hydrogenating dielectric fluid as recited in claim 1, wherein the catalyst is in solution with the dielectric fluid.

10. A method of hydrogenating dielectric fluid as recited in claim 9, wherein the effective amount of catalyst comprises about 0.01 gram per liter of the dielectric fluid up to about 1 gram per liter of the dielectric fluid.

11. A method of hydrogenating dielectric fluid as recited in claim 9, wherein the catalyst comprises at least one of the following: tris(triphenylphosphine) rhodium (I) chloride, precious metals in solution, and Wilkinson's catalyst.

12. A method of hydrogenating dielectric fluid as recited in claim 1, further comprising circulating the dielectric fluid through a mesh, wherein the mesh comprises the catalyst.

* * * * *